United States Patent [19]

Roux et al.

[11] Patent Number: 5,792,472
[45] Date of Patent: Aug. 11, 1998

[54] PROCESS FOR THE PREPARATION OF MICROCAPSULES OR LIPOSOMES OF CONTROLLED SIZES

[75] Inventors: Didier Roux, Merignac; Olivier Diat, Bordeaux; René Laversanne, Pessac, all of France

[73] Assignee: Capsulis, Pessac, France

[21] Appl. No.: 313,246

[22] PCT Filed: Apr. 2, 1993

[86] PCT No.: PCT/FR93/00335

§ 371 Date: Dec. 13, 1994

§ 102(e) Date: Dec. 13, 1994

[87] PCT Pub. No.: WO93/19735

PCT Pub. Date: Oct. 14, 1993

[30] Foreign Application Priority Data

Apr. 3, 1992 [FR] France .................. 92 04108

[51] Int. Cl.⁶ .................................................. A61K 9/127
[52] U.S. Cl. .................. 424/450; 428/402.2; 264/4.1; 264/4.3; 264/4.32; 424/489
[58] Field of Search ................... 426/450, 489; 264/4.3, 4.32, 4.6; 428/402.2

[56] References Cited

U.S. PATENT DOCUMENTS 5,091,111   2/1992   Neumiller ................. 252/305

FOREIGN PATENT DOCUMENTS

| 0 466 236 | 1/1992 | European Pat. Off. . |
| 4 038 075 | 3/1992 | Germany . |
| 1 376 166 | 12/1974 | United Kingdom . |
| WO 86/02264 | 4/1986 | WIPO . |

OTHER PUBLICATIONS

"Pharmazeutische Technologie", Georg Thieme Verlag, Stuttgart, Germany, 1991 by H. Sucker et al. pp. 5 and 6.
Fukuda, J. Am. Chem. Soc. 108, 2321–2327, 1986.

Primary Examiner—Gollamudi S. Kishore
Attorney, Agent, or Firm—Young & Thompson

[57] ABSTRACT

Process for the preparation of microcapsules with controlled sizes in which a homogeneous liquid crystal lamellar phase is prepared comprising at least one surfactant and at least one solvent and, if need be, one substance to be encapsulated. The invention is characterized in that the lamellar phase is subjected to constant shearing.

12 Claims, 2 Drawing Sheets

PROCESS FOR THE PREPARATION OF MICROCAPSULES OR LIPOSOMES OF CONTROLLED SIZES

This application is a 37 of PCT/FR93/00035 filed Apr. 2, 1993.

The subject of the present invention is a process for the preparation of microcapsules or liposomes of controlled size by application of a shearing having a constant shear rate to a lamellar phase.

Microcapsule is understood to mean a particle of micron size (0.1 to 10 µm), closed by one or a number of double layers (constituting the membrane) composed of at least one type of surface-active agent (molecule composed of a lipophile part and another hydrophile part which settles at interfaces). This or these membrane(s) enclose(s) in the space a volume of solvent, isolated from the remainder of the solution, which is the encapsulated volume. The encapsulation yield is defined as the percentage of encapsulated volume with respect to the total volume of solvent.

In the specific case of surface-active agents of lipid origins, especially phospholipids, these capsules are known as liposomes.

Many methods for the preparation of microcapsules and liposomes have been described in the literature. The methods proposed include especially methods based on the mechanical dispersion of the surface-active agent(s) in a solvent, methods for the preparation of emulsions of a volatile organic solvent in an aqueous solvent and then evaporation of the organic part, and methods by polymerization of a monomer such as acrylic acid (for example, BE-A-808,034, FR-A-2,504,408, U.S. Pat. No. 3,242,051 or U.S. Pat. No. 4,637,905).

In the case of liposomes, the processes described generally contain methods by emulsification (for example, FR-A-2,315,991, FR-A-2,399,242 and FR-A-2,521,565).

These methods lead, in the best cases, to encapsulation levels of the order of 50% and to relatively polydispersed particles.

The present invention proposes a simple method for the preparation of very concentrated monodispersed microcapsules at a very high encapsulation yield (more than 90%), while controlling very precisely the size of the microcapsules.

This result is obtained by subjecting a single-phase, liquid crystal, lamellar phase to a shearing having a constant shear rate which is homogeneous in space.

This result is astonishing because those skilled in the art would have logically thought that the application of a shearing having a constant shear rate to a lamellar phase would have led to an at least partial orientation of this phase rather than to the manufacture of small isotropic particles of given size.

The subject of the invention is therefore a process for the preparation of microcapsules of controlled sizes, in which a homogeneous, liquid crystal, lamellar phase is prepared comprising at least one surface-active agent and at least one solvent and, if appropriate, a substance intended to be encapsulated, characterized in that this lamellar phase is subjected to a shearing having a constant shear rate.

In a first stage, a homogeneous lamellar phase is prepared consisting of at least one type of surface-active agent (ionic or nonionic) in at least one type of solvent (especially water or a saline or alcoholic aqueous solution). A lamellar phase is defined by a regular stacking of membranes separated by a solvent. This is a liquid crystal phase (smectic-A), characterized by a solid nature in the direction perpendicular to the membranes and a liquid nature in the other two directions. The concentrations are chosen according to the phase diagram of the system which localizes the stability region of the lamellar phase. Generally, this lamellar phase exists in all the surface-active agents/water systems at high concentrations of surface-active agents (>30% by weight). In certain cases, this lamellar phase persists at much lower concentrations of surface-active agents (as far as less than 1–10%).

In practice, 0.5 to 50% by weight especially of surface-active agents with respect to the lamellar phase can be used. These surface-active agents can be both ionic (derivatives of optionally alkoxylated fatty acids, sulphonates, quaternary ammonium derivatives, and the like) and nonionic (polyethers, polyalcohols, and the like) and more generally any compound which can form a lamellar phase and will be chosen according to the applications of the product prepared.

Moreover, it is possible to prepare systems where the membrane consists of a thin film of water surrounded by two layers of surface-active agents (reverse membranes), everything being diluted in a hydrophobic solvent.

In the case where the membrane consists of water (reverse membrane), the solvent is chosen from hydrophobic liquids, especially aliphatic hydrocarbons ($C_5$ to $C_{25}$ in particular) or aromatic hydrocarbons, which are optionally halogenated, higher alcohols ($C_4$ to $C_{12}$ in particular), ketones, and the like.

This lamellar phase, once prepared, can be easily characterized by observation, under a polarized optical microscope, of the texture, thus showing flaws characteristic of the lamellar nature (focal conics, oily streaks). In the case of the concentrated phases (>20%), it is also possible to characterize it using X-rays. In the case of the dilute phases, it is possible to characterize the lamellar nature by neutron scattering or, in extreme cases, by light scattering.

In a second stage, which constitutes the main novel feature of the invention, this lamellar phase is subjected to a constant shear rate, in a suitable device. There currently mainly exist two types of devices which may be suitable for this purpose.

A first type of device is a cell, known as a Couette cell, consisting of two concentric cylinders in constant rotation with respect to one another, where the shear rate is defined by the ratio of the relative displacement rate divided by the distance between the cylinders. Another type of device is the cell of cone/plate type where a cone, whose point is directed towards a plate and whose axis is perpendicular to this plate, rotates at a constant angular velocity at a distance from the plate.

In the two devices described above, it is possible to show that the shear rate is constant throughout the cell. These cells are commonly used in commercial apparatuses, in particular rheometers, which make it possible to measure the viscoelastic properties of liquids (for example: Carrimed or Rheometrix). However, their application to the preparation of microcapsules has never been envisaged. Such apparatuses can be used for the preparation of microcapsules according to the invention.

The lamellar phase must be subjected to a constant shear rate for a certain time in order to obtain a stationary state. The kinetics of formation can be monitored by measuring, as a function of time, the torque which is applied to one of the cylinders for a prescribed rate of rotation of the other (i.e. shear rate). This is easily produced on the commercial apparatuses described above. The typical time for reaching the stationary state is of the order of a few minutes to a few hours (especially 1 min to 100 min); the higher the shear rate, the shorter the time required. The shear rate typically lies between 1 and 1000 s$^{-1}$, especially between 2 and 400 s$^{-1}$.

Once the shearing has stopped, a cream is recovered which consists of a dense assembly of small monodisperse spheres (spherical objects) of lamellar phases. These small spheres constitute the microcapsules whose size is a direct function of the shear rate which has been applied during the preparation. It can be shown experimentally and theoretically that the diameter varies as the inverse of the square root of the shear rate.

The size can be measured by various methods. The simplest is to withdraw a small amount of cream and to fill an optically transparent cell (1 to 10 mm Helma cell, for example). By sending a laser beam through the cell and by placing a screen on the path after the cell, a scattering ring is observed whose position directly gives the diameter D of the microcapsules by using the conventional formula:

$$D = \lambda/n/2/\sin(\theta/2)$$

θ being the angle formed by the position of the ring and the initial beam,

λ being the wavelength of the light, and n being the refractive index of the medium It is also possible to place the cream obtained under a polarizing microscope and to observe a homogeneous texture whose characteristic size is the diameter of the microcapsule.

It is alternatively possible to produce electron microscopy images under the same conditions as those which are used to characterize the liposomes.

The process according to the invention makes it possible to prepare microcapsules having sizes generally between 0.1 and 50 micrometers, more commonly between 0.8 and 8 micrometers, with less than 10% polydispersity by radius. It is suitable particularly for the preparation of liposomes.

In the undiluted state, these microcapsules are very stable and can be stored for a very long time depending on the surface-active agent used.

The microcapsules prepared in the cream form by the process according to the invention can subsequently the used directly to prepare a dilute solution of microcapsules by simple addition of solvent. The stability of the microcapsules in suspension is then identical to that obtained by other methods and is therefore a function of the system used.

It is possible to measure the encapsulation yield either directly on the cream, by a low-frequency conductivity method, for example, or by a conventional technique on a dilute solution of microcapsules. It is also possible to measure the encapsulation yield by incorporating a dye in the lamellar phase and by measuring, after shearing and centrifuging, the concentration of dye in the supernatant. An encapsulation of the order of 90 to 95% is generally obtained.

The process of preparation according to the invention therefore makes it possible to obtain microcapsules of controlled and monodispersed sizes. Moreover, a very high concentration of these particles is obtained. This set of properties makes it possible to easily determine the characteristic size by observation of a light-scattering ring or even by direct measurement under a phase-contrast microscope.

It is possible to explain the formation of these small spheres in the following way. When the shear rate is very small (typically<1 s$^{-1}$), the system of orientation of the lamellar phase obtained is that described by Oswald and Kléman (J. de physique lettres, 43, L-411, 1983) in the case of thermotropic smectic phases. Movement then takes place by fault slipping according to the laws for the lubrication of smectic materials. As soon as a critical shear rate (of the order of 1 s$^{-1}$) is exceeded, the movement imposed is too rapid to enable the dislocations to move and the system forms spherical objects of constant sizes which roll against each other. The size is fixed by an equilibrium between the elastic force necessary to maintain the system at a size D and the viscous force which is exerted on each of the particles by its moving neighbours. It can then be shown that:

$$D = \sqrt{\frac{4\pi(2k_c + \bar{k})}{\eta d \dot{\gamma}}}$$

with $k_c$ and $\bar{k}$ which are respectively the elastic constants of the mean and Gaussian curvatures of the membrane, η is the viscosity of the medium $\dot{\gamma}$ is the shear rate.

d is the distance between membranes in the starting lamellar phase.

Independently of the encapsulation properties described above, the cream obtained is a threshold viscoelastic medium.

The relationship which exists between the size of the microcapsules obtained and the shear rate applied shows that it is possible to adjust the size depending on the applications. This also makes it possible to modify the viscoelastic properties of the system, without changing its composition, simply by modifying the value of the shear rate. It is thus possible to prepare viscoelastic fluids having different viscoelastic frequencies, the viscoelastic frequency being defined as the frequency at which the elastic and viscous moduli intersect.

In an advantageous embodiment of the invention, a monomer is incorporated in the liquid crystal lamellar phase before shearing, this monomer being in the dissolved state in one of the constituents of this lamellar phase, and polymerization of the monomer is initiated after the shearing stage.

The monomer can, for example, be either dissolved in the water (for example acrylamide or a derivative of acrylic acid) or dissolved in the oil (styrene, for example) or, if it has surface-active properties, dissolved in the surface-active agent membrane. It is also possible to use the monomer in the pure state in order to replace one of the constituents of the lamellar phase. This is the case, for example, for the oil, which can be pure styrene, or for the surface-active agent, which can be a polymerizable surface-active agent used pure. Generally, a crosslinking agent is added which makes it possible to obtain a stable polymer gel.

Depending on the nature of the initiation reaction of the polymerization, it may be necessary to add a chemical initiator. It is necessary, in this case, to add it before the shearing stage, in order to ensure that it is homogeneously dissolved. It is then possible to trigger the polymerization reaction by modifying an external parameter (for example, by heating or exposure to ultraviolet radiation), avoiding any initiation of the reaction during the preparation stage of the microcapsules.

In the same way, if it is desired to encapsulate an active principle, it must be dissolved in the lamellar phase before it is sheared.

This phase, containing the active principle, the monomer and the initiator, is subjected to a shear rate, by the process according to the invention, which is constant for the time necessary to obtain the stationary state. This constitutes the first stage. On conclusion of this treatment, the cream obtained is recovered.

In a second stage, this cream is polymerized. The polymerization can be carried out either on the pure cream or on the cream diluted in the solvent which has been used for the manufacture of the liquid crystal phase. The triggering of the polymerization reaction makes it possible to obtain polymerized microcapsules. These microcapsules can then be diluted or used as is.

These polymerized microcapsules are characterized, inter alia, by a much greater stability than that of the unpolymerized capsules (no degradation after several months) and a significant slowing-down in escape of the active principle enclosed in the capsules.

In certain cases, these microparticles can be dispersed, both in an aqueous or in an organic solvent.

In another embodiment of the invention, use is made, as lamellar phase, of a phase which is capable of changing from the state of a liquid crystal lamellar phase (Lα phase) to a gel phase (Lβ phase) at lower temperature where the surface-active agent molecules are arranged according to a solid two-dimensional nature in each membrane and, after shearing, the microcapsules are brought to a temperature below the gel/liquid phase transition temperature.

This phase transition is well known both in lipid systems and for synthetic surface-active agents.

The microcapsules are prepared in the liquid crystal lamellar phase (high-temperature phase) by following the process described previously. The principles of formation and the results are similar to those described previously. The cream of concentrated microcapsules is then brought to a temperature below that of the gel/liquid transition. A concentrated cream of microcapsules solidified in the gel phase is thus obtained. These microcapsules can then be diluted in a solvent. If an active principle is added during the preparation of the starting liquid crystal phase, this active principle is found in the solid capsules on conclusion of the preparation. By reheating the dilute suspension of solid capsules above the gel/liquid transition temperature, this principle is then released according to kinetics related to the composition of the membrane in the liquid crystal phase.

The property of certain physical gels of reversibly changing from the liquid state to the gel state as a function of temperature can also be used to make possible the manufacture of gelled microparticles. It is thus possible to prepare a liquid crystal phase with the gelling polymer in the solvent. This phase is sheared above the gelling temperature of the polymer and then, after obtaining the microcapsules, cooled to below the gelling temperature. The capsules obtained can then be dispersed in a solvent. By repeating the gel/liquid transition in the reverse direction, it is thus possible to control the release of an active principle (encapsulated during the preparation).

It is additionally possible to couple the process according to the invention to a conventional encapsulation process: coacervation. Coacervation usually consists, in a first stage, in preparing an emulsion of a hydrophobic liquid in water. A polymer is then adsorbed at the oil/water interface to form a polymerized shell which makes it possible to stabilize this emulsion. A hydrophobic active principle is thus encapsulated in a hydrophilic capsule by this process. Moreover, the size of the microcapsules thus obtained is relatively large (10–1000 μm).

If the same method is applied in a second stage of the process according to the invention, it is possible to encapsulate a hydrophilic compound in a hydrophilic matrix (or a hydrophobic compound in a hydrophobic capsule). Moreover, the size is well controlled and can fall below one micron.

It is additionally possible to use the process according to the invention to prepare solid particles. To this end, the process according to the invention is used as a preparatory stage of a chemical microreactor in order to prepare, for example, solid particles of controlled size. The process will be illustrated by the preparation of monodispersed nickel particles. Two methodologies are applied. If a chemical reaction consists in reacting a molecule A with a molecule B (or an array of molecules), one of the reactants can be encapsulated in the microcapsules and these capsules can be dispersed in a solvent containing the reactant B. The reaction is then triggered in the capsule which is being used as container (microreactor). If this reaction consists in the production of a polymerized or solid product AB, the size of the resulting object is then controlled by the amount of reactive product in the capsule, by the number of reactive sites and by the concentration of the reactant outside the capsule. It is also possible, in the case of a catalytic reaction, to encapsulate the catalyst in the capsule and to place all the reactants (except for the catalyst) in the solvent which is being used as diluent. The dispersion of the capsules containing the catalyst in the solvent containing the reactants leads to the triggering of the reaction within each capsule. If solid or polymerized capsules are prepared, it is again possible thus to control the size of the resulting particles.

The process for the preparation of microcapsules according to the invention finds applications in many fields.

1) Paints

The process can be used at a number of levels in the preparation of paints. It is possible to encapsulate an active principle and to dilute these capsules in a paint. The release of this active principle is controlled at the oil/water interface to form a polymerized shell which makes it possible to stabilize this emulsion. A hydrophobic active principle is thus encapsulated in a hydrophilic capsule by this process. Moreover, the size of the microcapsules thus obtained is relatively large (10–1000 μm).

If the same method is applied in a second stage of the process according to the invention, it is possible to encapsulate a hydrophilic compound in a hydrophilic matrix (or a hydrophobic compound in a hydrophobic capsule). Moreover, the size is well controlled and can fall below one micrometer.

It is additionally possible to use the process according to the invention to prepare solid particles. To this end, the process according to the invention is used as a preparatory stage of a chemical microreactor in order to prepare, for example, solid particles of controlled size. The process will be illustrated by the preparation of monodispersed nickel particles. Two methodologies are applied. If a chemical reaction consists in reacting a molecule A with a molecule B (or an array of molecules), one of the reactants can be encapsulated in the microcapsules and these capsules can be dispersed in a solvent containing the reactant B. The reaction is then triggered in the capsule which is being used as container (microreactor). If this reaction consists in the production of a polymerized or solid product AB, the size of the resulting object is then controlled by the amount of reactive product in the capsule, by the number of reactive sites and by the concentration of the reactant outside the capsule. It is also possible, in the case of a catalytic reaction, to encapsulate the catalyst in the capsule and to place all the reactants (except for the catalyst) in the solvent which is being used as diluent. The dispersion of the capsules containing the catalyst in temperature below 30°/35° C. The viscoelastic properties can help in the formulation of beauty creams.

5) Liquid detergents

In the field of liquid detergents, consideration may be given to using the process according to the invention in order to control chemical reactions which have to take place during the washing. These microcapsules can also form part of the composition of conditioners (in particular those giving Lβ solid phase capsules).

6) Agricultural foodstuffs

In the farm-produce field, the process can be used as an alternative to polymer-based processes. It will be noted that the very high encapsulation level and the precise control of the size are significant assets. The active principles to be encapsulated are flavourings or any other product requiring specific protection (sweeteners, for example).

7) Biomedical/pharmaceutical

In the biomedical and pharmaceutical field, the process can be applied in many ways.

Encapsulation of medicinal active principles or biological substances can be obtained by dissolving one or a number of active principles in the starting lamellar phase. These active principles are thus found encapsulated within the microcapsules in the proportion of the encapsulation yield.

Moreover, mention may be made, as examples, of the vectorization of medicaments, the development of contrast agents for medical imaging (magnetic products for magnetic resonance imaging) or preparation of artificial blood (by using fluorinated surface-active agents). It is also possible to use this process in the preparation of medical tests (for example, by using polymerization).

8) Hydraulic binders

The process makes it possible, for example, to prepare a delay catalyst for the rapid setting of materials such as cements, concrete, plaster and the like. By encapsulating this catalyst by the process according to the invention, it is possible to delay its effect. This makes possible the use of the material and the delayed triggering of setting due to the controlled escape of the catalyst.

A BRIEF DESCRIPTION OF THE DRAWINGS

The following examples illustrate the invention with the appended figures in which.

EXAMPLE 1

Ionic surface-active agent+salt water

Figure 1:
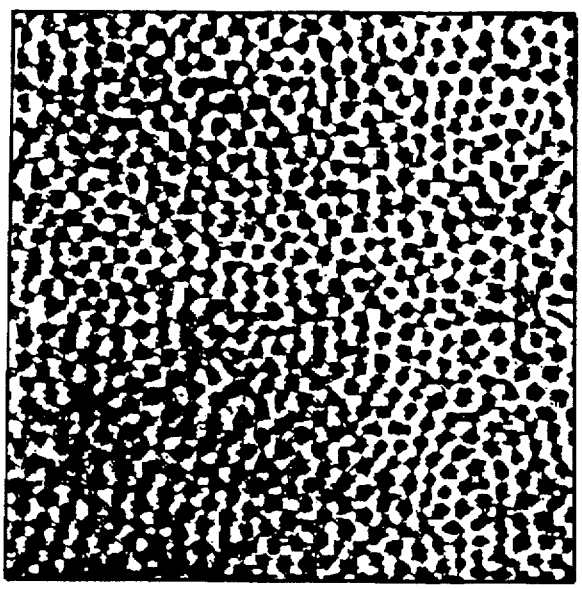
FIG. 1 is a phase-contrast-microscope photograph of microcapsules obtained according to the process of the invention.

A lamellar phase is prepared by dissolving 16.8% of an ionic surface-active agent, dioctyl sodium sulphosuccinate (Aerosol OT of the company Sigma Chemical Co), in 83.2% of salt water (12 g/l sodium chloride). This lamellar phase is then subjected to a constant shear rate of 3 $s^{-1}$ for 30 min using a rheometer (Carrimed 50) equipped with a Couette-Mooney cell. The cream obtained is decanted into a transparent 1 mm cell placed in a laser beam. The size of the scattering ring observed indicates that the microcapsules obtained have a diameter of 2 μm with a polydispersity of approximately 10%. It is possible to observe, under a polarizing microscope, a homogeneous texture of a characteristic size of 2 μm. It is possible to dilute this cream in 12 g/l salt water and to observe, under a phase-contrast microscope, a more or less concentrated solution of microcapsules (FIG. 1).

EXAMPLE 2

Variation in size of the microcapsules as a function of the shear rate

Figure 2:
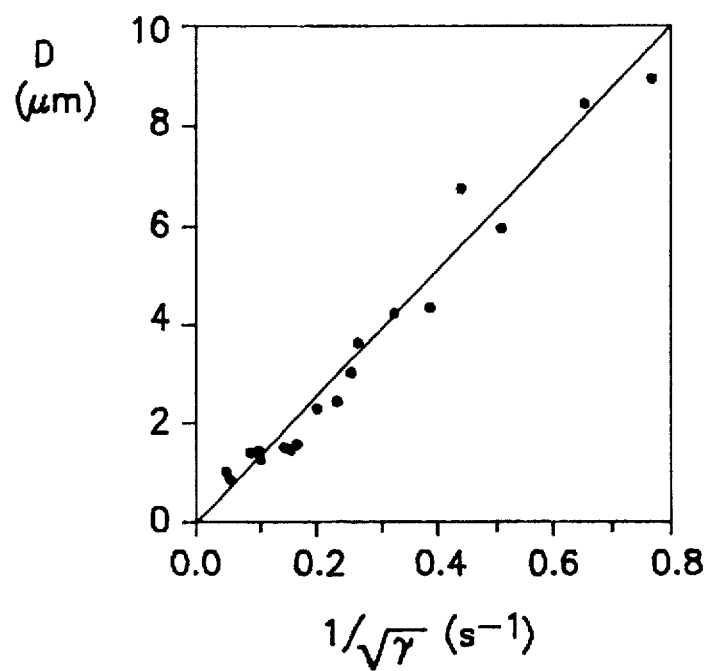
FIG. 2 represents the measurement of the size of the microcapsules as a function of the shear rate applied according to the process of the invention.

A lamellar phase is prepared by dissolving 17% of ionic surface-active agent (Aerosol OT of the company Sigma) in 83% of salt water (15 g/l sodium chloride). This lamellar phase is then subjected to a shear rate varying from 2 to 400 $s^{-1}$, as in Example 1. The size of the microcapsules is measured by light scattering; the curve shown in the appended FIG. 2 is obtained. The size (diameter) varies linearly as a function of the inverse of the square root of the shear rate from 8 μm to 0.8 μm.

EXAMPLE 3

Reverse membrane

A reverse lamellar phase in prepared by mixing 14.85% of pentanol, 13.77% of SDS (sodium dodecyl sulphate), 50.06% of dodecane and 21.32% of water and homogenization. After having left standing, this lamellar phase is composed of water films surrounded by surface-active agents with a thickness of 20 Å and separated by a solvent composed of dodecane and pentanol with a thickness of 90 Å (characterization obtained by measuring the Bragg peak by X-ray diffraction). This phase is subjected to a constant shear rate (between 3 $s^{-1}$ and 280 $s^{-1}$). At each shear rate, the size in the stationary state is measured by light scattering. A size varying from D=1 μm to 6 μm as a function of the shear rate is obtained.

EXAMPLE 4

Nonionic surface-active agent+alcohol+pure water

A lamellar phase composed of 16% (by weight) of surface-active agent C 12 E5 (pentaethylene glycol mono n-dodecyl ether of the company Nikkol), 4.25% of hexanol and 79.75% of water is prepared and then subjected to a shear rate at 2 $s^{-1}$ for 10 min. A cream composed of small spheres having a diameter of 2 μm is obtained which can be measured by light scattering by the method described in Example 1. Variation of the shear rate from 1 $s^{-1}$ to 10 $s^{-1}$ makes it possible to obtain sizes varying from 1.5 to 8 μm.

EXAMPLE 5

Ionic surface-active agent+pure water

A very dilute phase containing DDAB (didodecyldimethylammonium bromide of the company Aldrich) in pure water is prepared (5% of DDAB in 95% of water), which corresponds to a distance between membranes of 800 Å (measured by neutron scattering). This phase, subjected to a constant shear rate of 10 $s^{-1}$ for 30 min, results in a concentrated phase of small spheres with a diameter of approximately 1 μm.

EXAMPLE 6

Lecithin+cholesterol+water

A mixture of 47% by weight of soya lecithin (Cernes Synthelabo), 13% of cholesterol and 40% of water is prepared and then subjected to a constant shear rate at 400 s$^{-1}$ for 10 min. A phase is obtained of concentrated microcapsules with a diameter of 2 μm. It is possible to disperse these small spheres in pure water and to observe the Brownian motion of these liposomes and their size with a phase-contrast microscope. By varying the shear rate from 300 to 700 s$^{-1}$, the size of the liposomes can be varied from 3 to 1 μm.

EXAMPLE 7

Diagram for the formation of microcapsules

In order to determine the possibility of formation of microcapsules for a given system, it is possible to draw up a directional diagram which delimits the region of existence of these microcapsules as a function of the shear rate and of other parameters which can be experimentally varied. By way of example, a system identical to Example 3 was systematically studied. The region of formation of microcapsules was localized as a function of two parameters: the shear rate and the degree of dilution of the lamellar phase which determines the distance between membranes. The starting reverse lamellar phase contains: 22% of pentanol, 31% of SDS and 47% of water. This phase is diluted with a mixture of 91% of dodecane and 9% of pentanol. The lamellar phase is stable from 0% of dodecane to 80% of dodecane.

Figure 3A:
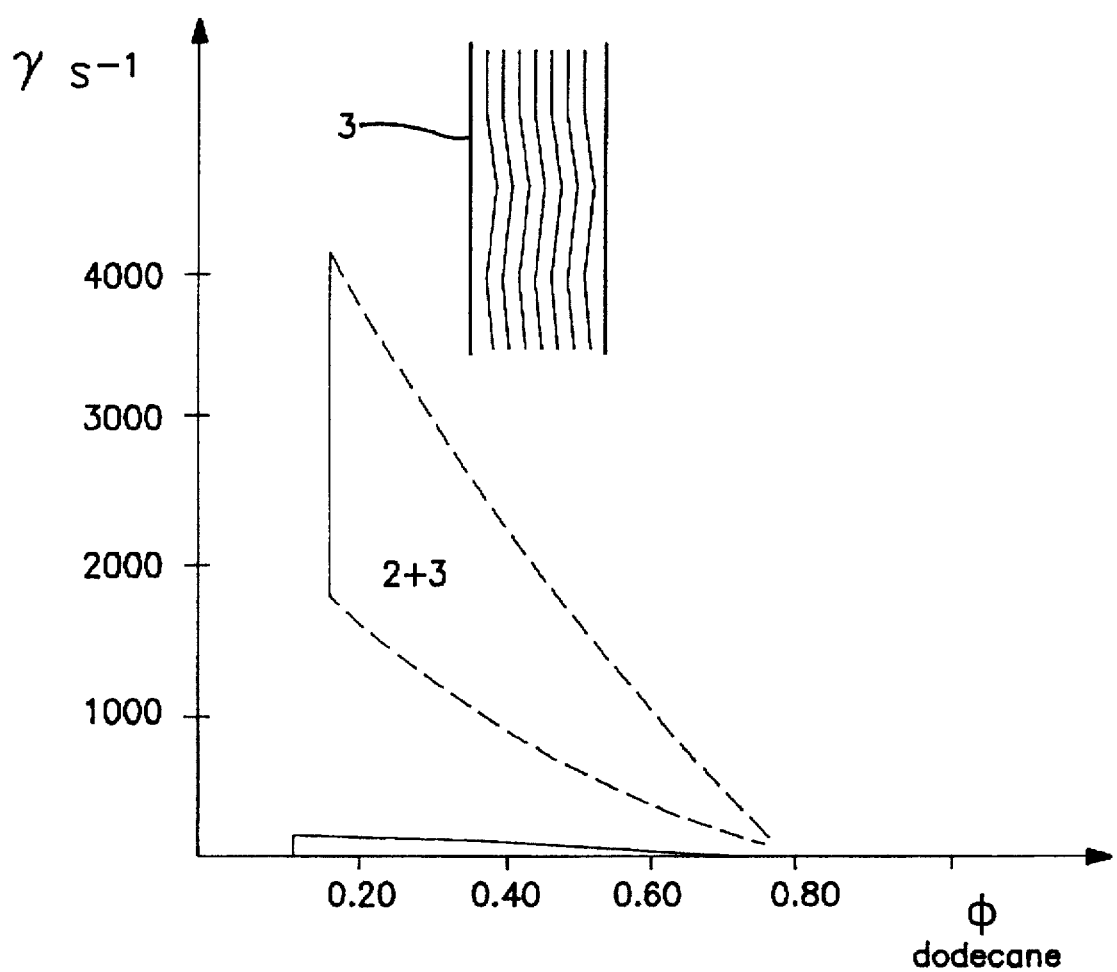
FIG. 3 is a diagram corresponding to the region of formation of the microcapsules as a function of the proportion of solvent and of the shear rate.
Figure 3B:
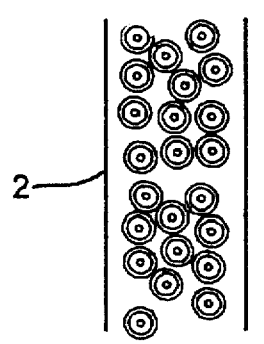
Figure 3C:
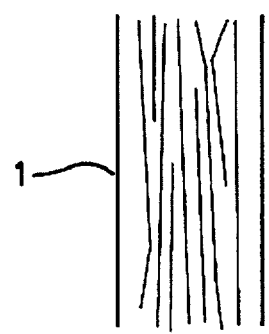

The appended FIG. 3 represents the region of formation of the microcapsules as a function of the fraction, by volume, of dodecane and of the shear rate. This diagram was obtained with a 2 mm Couette cell. In this figure, the region 2 where the microcapsules are formed is limited by two lines which correspond respectively to a region which is, taken as a whole, oriented with the membranes parallel to the direction of flow with faults (region 1 at low shear rate) or faultless (region 3 at high shear rate) in this direction.

EXAMPLE 8

Preparation of polymerized microcapsules

A lamellar phase is prepared containing by weight: 30% of Aerosol OT, 60% of salt water (15 g/l of NaCl), 9% of acrylamide and 1% of methylenebisacrylamide (crosslinking agent). 50 μl of a solution of triethanolamine (60 g.l$^{-1}$) in water and 50 μl of a solution containing 0.2 g.l$^{-1}$ of methylene blue and 0.2 g.l$^{-1}$ of eosine (initiator of the polymerization reaction in the presence of light) are added to 1 g of this preparation. Care is taken not to expose the mixture to light during the preparation stage of the microcapsules. This liquid crystal phase is placed in a Couette (or cone/plate) cell and subjected to a constant shear rate of 20 s$^{-1}$ for 2 hours. After this stage, the cream thus obtained is placed in a quartz cell and subjected to luminous radiation (sunlight or mercury vapour lamp) for a few minutes. A progressive decoloration then takes place, indicating consumption of the initiators and initiation of the reaction. A cream of polymerized microcapsules is then recovered. These microcapsules can be diluted in a salt water solution (15 g/l) and observed under an optical microscope. It is also possible to dilute these microcapsules in cyclohexane. Small polymer capsules in suspension in a reverse phase are then obtained. Measurement by dynamic light scattering indicates that these particles have a diameter of 0.2 μm.

As a variant, it is possible to dilute the cream by a factor of 2 (in salt water containing 15 g/l of NaCl) before carrying out the polymerization stage. Similar microcapsules are then obtained.

EXAMPLE 9

Preparation of polymerized microcapsules

A mixture containing 30% of Aerosol OT, 50% of salt water (15 g/l of NaCl), 15% of acrylamide and 5% of methylenebisacrylamide (crosslinking agent) is prepared. 50 μl of a solution of triethanolamine (60 g.l$^{-1}$) in water and 50 μl of a solution containing 0.2 g.l$^{-1}$ of methylene blue and 0.2 g.l$^{-1}$ of eosine (initiator of the polymerization reaction in the presence of light) are added to 1 g of this preparation. This phase is subjected to shearing and then to the action of ultraviolet radiation and microparticles are obtained. These microcapsules are more stable than in Example 8 and their size remains constant with time.

EXAMPLE 10

Preparation of phase transition microcapsules

A phase containing by weight 10% of SDS (sodium dodecyl sulphate), 10% of dodecanol and 80% of 20 g/l salt water is prepared (an active principle, for example calcein (fluorescent agent) can be added to this water in order to demonstrate the effect indicated). This phase is sheared at a temperature of 50° C. for 15 min at a shear rate of 20 s$^{-1}$. The cream withdrawn is then cooled to a temperature of 20° C. The capsules obtained can then be diluted in a salt water phase (20 g/l) and a suspension of solid particles with the active principle encapsulated is obtained. By reheating this suspension above the gel point (approximately 40° C.), the latter is released. In the case where the active principle is calcein, the release can be monitored by fluorescence with the presence of an agent which inhibits fluorescence in the water of dilution (cobalt salt, for example).

EXAMPLE 11

Preparation of colloidal nickel particles of controlled size 0.1 ml of a 10$^{-2}$M solution of sodium tetrachloropalladate is added to 1 g of a lamellar phase containing 17% by mass of Aerosol OT and 83% of 15 g/l salt water. This phase is sheared at 4 s$^{-1}$ for 2 h. 0.2 g of the cream of small spheres obtained is dispersed in 2 ml of 15 g/l salt water and then 1 ml of a 5% by mass solution of dimethylaminoborane is added thereto. After a few minutes, 1 ml of a solution containing 0.1 mol/l of nickel(II) chloride, 0.1 mol/l of sodium gluconate, 0.2 mol/l of sodium hypophosphite and 3.8% by volume of concentrated ammonia is added. The solution darkens immediately and gas evolution appears. The nickel particles can be collected by centrifuging. Study by X-ray diffraction indicates a size of 300±25 Å.

We claim:

1. Process for the preparation of microcapsules of controlled sizes, comprising subjecting to shearing in a shearing cell at a shear rate that is constant throughout said cell, a single-phase, homogeneous, liquid crystal, lamellar phase selected from the group consisting of a lamellar phase composed of a stack of membranes comprising at least one surface active agent separated by an aqueous solvent and a lamellar phase composed of a stack of reverse membranes formed from water surrounded by two layers of at least one surface active agent separated by a hydrophobic solvent.

2. Process according to claim 1, in which the aqueous solvent is water or an aqueous saline solution.

3. Process according to claim 1, in which the microcapsules are liposomes.

4. Process according to claim 1, in which the lamellar phase comprises said reverse membranes.

5. Process according to claim 1, in which the surface-active agent(s) constitute(s) from 0.5 to 50% by weight of the lamellar phase.

6. Process according to claim 1, in which the shear rate is between 1 and 1000 s$^{-1}$.

7. Process according to claim 6, in which the shear rate is between 2 and 400 s$^{-1}$.

8. Process according to claim 1, in which the constant shear rate is produced using a cell consisting of two concentric cylinders in constant rotation with respect to one another.

9. Process according to claim 1, in which the constant shear rate is produced using a device comprising a cone and a plate in which the apex of the cone is directed toward the plate and whose axis is perpendicular to said plate.

10. Process according to claim 1, in which a monomer is incorporated in the liquid crystal lamellar phase before shearing, this monomer being in the dissolved state in one of the constituents of this lamellar phase, and the polymerization of the monomer is initiated after the shearing.

11. Process according to claim 1, wherein the lamellar phase is one capable of changing to a gel phase state at low temperature and wherein after shearing, the microcapsules are brought to a temperature below the gel/liquid phase transition temperature.

12. Process according to claim 1, in which the microcapsules have a diameter of 0.1 to 10 μm.

* * * * *